United States Patent [19]

Lohmann et al.

[11] Patent Number: 5,990,345
[45] Date of Patent: Nov. 23, 1999

[54] PROCESS FOR PREPARATION OF ETHYLENICALLY UNSATURATED ISOCYANATES

[76] Inventors: Dieter Lohmann, Mittelweg 56, 4142 Münchenstein; Rudolf Duthaler, Girenhaldenweg 17, 4126 Bettingen, both of Switzerland

[21] Appl. No.: 08/982,654

[22] Filed: Dec. 2, 1997

[30] Foreign Application Priority Data

Dec. 19, 1996 [EP] European Pat. Off. .............. 96810882

[51] Int. Cl.$^6$ .................................................. C07C 263/00
[52] U.S. Cl. ........................... 560/345; 560/215; 560/222
[58] Field of Search .................................... 560/345, 215, 560/222

[56] References Cited

U.S. PATENT DOCUMENTS 4,707,466  11/1987  Engel et al. ............................ 558/411

OTHER PUBLICATIONS

Chemical Abstracts, Synthetic High Polymers, vol. 106, 1987, sectioni 106:102820s pp. 9–10 and DE–A–3,523,692.

Derwent Abstract AN 70–20886R.

*Primary Examiner*—Samuel Barts
*Attorney, Agent, or Firm*—Michael U. Lee

[57] ABSTRACT

A process for the preparation of ethylenically unsaturated isocyanates is described, which process comprises silylating an appropriate ethylenically unsaturated urethane precursor at the urethane nitrogen and converting the resulting unsaturated N-silyl-urethane by means of thermolysis at elevated temperature into the desired isocyanate. The unsaturated isocyanates obtainable according to the process are suitable, for example, as monomers or comonomers in the preparation of polymerisates or copolymerisates.

15 Claims, No Drawings

PROCESS FOR PREPARATION OF ETHYLENICALLY UNSATURATED ISOCYANATES

The present invention relates to a process for the preparation of ethylenically unsaturated isocyanates, especially vinyl isocyanates, vinylbenzyl isocyanates or isocyanato esters of unsaturated organic acids, for example isocyanatoalkyl (meth)acrylates.

Isocyanatoalkyl (meth)acrylates are known compounds and are customarily prepared using phosgene. For example, an industrial synthesis of isocyanatoethyl methacrylate (IEM) is performed by cyclising N-2-hydroxyethyl methacrylamide (obtained from the reaction of ethanolamine with methyl methacrylate) in sulfolane at temperatures above 200° C. to form 2-isopropenyl-oxazoline and reacting the resulting compound with phosgene to form the isocyanato compound. Various attempts at avoiding the use of phosgene, which is toxic and can be handled only using apparatus-intensive means, have so far not met with the desired success. There is therefore a need for a phosgene-free, gentle synthesis of isocyanatoalkyl (meth)acrylates and related compounds. It has now been found, surprisingly, that certain ethylenically unsaturated isocyanates can be advantageously obtained by N-silylation of appropriate urethane precursors and subsequent thermal treatment under mild conditions.

The present invention therefore relates to a process for the preparation of ethylenically unsaturated isocyanates, which process comprises silylating an appropriate ethylenically unsaturated urethane precursor at the urethane nitrogen and converting the resulting ethylenically unsaturated N-silyl-urethane into the desired isocyanate by means of thermolysis.

More specifically, the present invention relates to a process for the preparation of compounds of formula

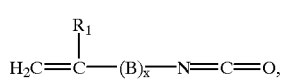  (1)

wherein $R_1$ is hydrogen or methyl,
x is the number 0 or 1,
B is phenylene or $C_7$–$C_{12}$aralkylene each of which is unsubstituted or substituted by $C_1$–$C_4$alkyl or by $C_1$–$C_4$alkoxy or is a radical of formula

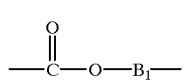  (2)

and $B_1$ is linear or branched $C_2$–$C_{12}$alkylene that is uninterrupted or is interrupted by one or more oxygen atoms, which process comprises converting an ethylenically unsaturated urethane of formula

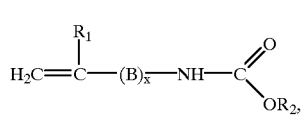  (3)

wherein $R_2$ is $C_1$–$C_4$alkyl or is phenyl that is unsubstituted or substituted by $C_1$–$C_4$alkyl, $C_1$–$C_4$alkoxy or by halogen and the variables $R_1$, B and x are as defined above, with the aid of a silylating agent, into an ethylenically unsaturated N-silyl-urethane of formula

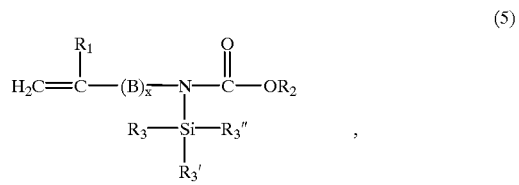  (5)

wherein $R_3$, $R_3'$ and $R_3''$ are each independently of the others $C_1$–$C_4$alkyl and the variables $R_1$, $R_2$, B and x are as defined above, and converting that compound at elevated temperature into an ethylenically unsaturated isocyanate of formula (1).

$C_1$–$C_4$alkyl is to be understood above as being generally methyl, ethyl, n- or iso-propyl or n-, iso-, sec- or tert-butyl, preferably methyl or ethyl, especially methyl. $C_1$–$C_4$alkoxy includes generally methoxy, ethoxy, n- or iso-propoxy and n-, iso-, sec- or tert-butoxy, preferably methoxy or ethoxy, especially methoxy. Halogen is generally, for example, fluorine, bromine, iodine or chlorine, preferably bromine or chlorine, especially chlorine.

$R_1$ is hydrogen or, preferably, methyl.

The variable x is, for example, the number 0 or, preferably, the number 1.

B as a phenylene radical is, for example, 1,2-, 1,3- or 1,4-phenylene that is unsubstituted or substituted by methyl or by methoxy. B as a phenylene radical is preferably 1,3- or 1,4-phenylene.

B as an aralkylene radical is, for example, benzylene that is unsubstituted or substituted by methyl or by methoxy, the methylene group in each case being bonded to the isocyanato nitrogen. B as an aralkylene radical is preferably the 1,3- or 1,4-phenylenemethylene radical, the methylene group in each case being bonded to the isocyanato or urethane nitrogen.

When B is a radical of formula (2) above, $B_1$ may be, for example, 1-methyl- or 1,1-dimethyl-methylene, 1,2-ethylene, 1,2- or 1,3-propylene, 2-methyl-propylene, or 1,2-, 1,3-, 1,4- or 2,3-butylene, 2,2-dimethyl-1,3-propylene, 2-methyl- or 2,3-dimethyl-1,4-butylene, 1,2-, 1,3-, 1,4- or 1,5-pentylene, 2-methyl- or 3-methyl- or 4-methyl-pentylene, or 1,2-, 1,3-, 1,4-, 1,5- or 1,6-hexylene, 2,3-dimethyl- or 2,4-dimethyl- or 3,4-dimethyl- or 2,3,4-trimethyl- or 2,2,3-trimethyl- or 2,2,4-trimethyl- or 2,2,3,3-tetramethyl- or 2,2,3,4-tetramethyl-1,5-pentylene, 2-methyl- or 3-methyl- or 4-methyl- or 2,2-dimethyl- or 3,3-di methyl- or 2,3-dimethyl- or 2,4-dimethyl- or 3,4-dimethyl- or 2,2,3-trimethyl- or 2,2,4-trimethyl- or 2,2,5-trimethyl- or 2,3,4-trimethyl- or 2,2,4,5-tetramethyl-1,6-hexylene, 1,2-, 1,3-, 1,4-, 1,5- or 1,6-heptylene, 2-methyl- or 3-methyl- or 4-methyl- or 5-methyl- or 2,2-dimethyl- or 3,3-dimethyl- or 2,3-dimethyl- or 2,4-dimethyl- or 3,4-dimethyl- or 2,2,3-trimethyl- or 2,2,4-trimethyl- or 2,2,5-trimethyl- or 2,2,6-trimethyl- or 2,3,4-trimethyl- or 2,4,5-trimethyl- or 2,4,6-trimethyl- or 2,2,4,5-tetramethyl-1,7-heptylene, 1,2-, 1,3-, 1,4-, 1,5-, 1,6- or 1,7-octylene, 2-methyl- or 3-methyl- or 4-methyl- or 5-methyl- or 6-methyl- or 7-methyl- or 2,2-dimethyl- or 3,3-dimethyl- or 2,3-dimethyl- or 2,4-dimethyl- or 3,4-dimethyl- or 2,6-dimethyl- or 2,7-dimethyl- or 2,2,4-trimethyl- or 2,2,5-trimethyl- or 2,2,6-trimethyl- or 2,2,5,6-tetramethyl-1,8-octylene, 1,2-, 1,3-, 1,4-, 1,5-, 1,6-, 1,7- or 1,8-nonylene, 2-methyl- or 3-methyl- or 4-methyl- or 5-methyl- or 6-methyl- or 7-methyl- or 8-methyl- or 2,2- dimethyl- or 3,3-dimethyl- or 2,3-dimethyl- or 2,4-dimethyl- or 3,4-dimethyl- or 2,6-dimethyl- or 2,7-dimethyl- or 2,8-dimethyl- or 2,2,4-trimethyl- or 2,2,5-trimethyl- or 2,2,6-trimethyl- or 2,2,7-trimethyl- or 2,2,8-trimethyl-nonylene, 1,2-, 1,3-, 1,4-, 1,5-, 1,6-, 1,7-, 1,8- or 1,9-decylene, 2-methyl- or 3-methyl- or 4-methyl- or 5-methyl- or 6-methyl- or 7-methyl- or 8-methyl- or 9-methyl- or 2,2-dimethyl- or 3,3-dimethyl- or 2,3-dimethyl- or 2,4-dimethyl- or 3,4-dimethyl- or 2,6-dimethyl- or 2,7-dimethyl-, 2,8-dimethyl- or 2,9-dimethyl-1,10-decylene, 1,2-, 1,3-, 1,4-, 1,5-, 1,6-, 1,7-, 1,8-, 1,9- or 1,10-undecylene, 2-methyl- or 3-methyl- or 4-methyl- or 5-methyl- or 6-methyl- or 7-methyl- or 8-methyl- or 9-methyl- or 10-methyl-1,11-undecylene, 1,4-, 1,5-, 1,6-, 1,7-, 1,8-, 1,9-, 1,10- or 1,11-dodecylene.

Examples of alkylene interrupted by oxygen atoms are —CH$_2$CH$_2$—O—CH$_2$CH$_2$—, —CH$_2$CH$_2$—O—CH$_2$CH$_2$—O—CH$_2$CH$_2$—, —CH$_2$CH$_2$—O—CH$_2$CH$_2$—O—CH$_2$CH$_2$—O—CH$_2$CH$_2$—, [—CH(CH$_3$)CH$_2$—O—CH(CH$_3$)CH$_2$—], —CH(CH$_3$)CH$_2$—O—CH$_2$CH$_2$—, —CH(C$_2$H$_5$)CH$_2$—O—CH$_2$CH$_2$—, [—CH(C$_2$H$_5$)CH$_2$—O—CH(C$_2$H$_5$)CH$_2$—] and —CH$_2$CH$_2$CH$_2$CH$_2$—O—CH$_2$CH$_2$CH$_2$CH$_2$—.

$B_1$ is preferably linear or branched $C_2$–$C_8$alkylene, especially linear $C_2$–$C_8$alkylene, more especially linear $C_2$–$C_4$alkylene. In a preferred embodiment of the invention, $B_1$ is 1,2-ethylene.

B is preferably a radical of formula (2) above, wherein the variable $B_1$ has the definitions and preferred meanings given above.

Preferably, $R_2$ is $C_1$–$C_2$alkyl or is phenyl that is unsubstituted or substituted by methyl, methoxy or by chlorine; $R_2$ is especially methyl, ethyl or phenyl. Examples of especially preferred radicals $R_2$ are ethyl and, more especially, phenyl.

Suitable for the silylation of the unsaturated urethane precursors is, in principle, any silylating agent customarily used, as known, for example, from A. E. Pierce, Silylation of Organic Compounds, Pierce Chemical Corp. Rockford Ill. 1968, pages 7–26. Examples of suitable silylating agents are alkylsilyl halides, alkylsilylamines, hexaalkyl-disilazanes and N-silylacetamides.

The silylating agent corresponds, for example, to formula

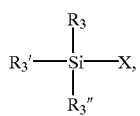

(4a)

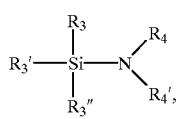

(4b)

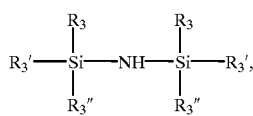

(4c)

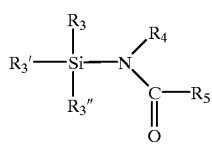

(4d)

or

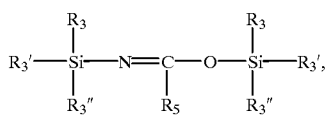

(4e)

wherein X is halogen, for example bromine or chlorine, preferably chlorine, $R_3$, $R_3'$ and $R_3''$ are each independently of the others $C_1$–$C_4$alkyl, preferably methyl or ethyl, especially methyl, $R_4$ and $R_4'$ are each independently of the other hydrogen or $C_1$–$C_4$alkyl, preferably hydrogen, methyl or ethyl, and $R_5$ is $C_1$–$C_4$alkyl, preferably methyl or ethyl, especially methyl.

In formulae (4a) to (4e), the variables $R_3$, $R_3'$ and $R_3''$ are different or, preferably, identical.

Examples of preferred silylating agents are trimethyl- or triethyl-silyl bromide, trimethyl- or triethyl-silyl chloride, hexamethyldisilazane, N-trimethylsiiyl-N,N-diethylamine, N-trimethyl-silyl-N-methylamine, N,O-bis(trimethylsilyl)acetamide and N-trimethylsilyl-N-methyl-acetamide. Especially preferred silylating agents are trimethylsilyl chloride, hexamethyl-disilazane, N-trimethylsilyl-N,N-diethylamine, N,O-bis(trimethylsilyl)acetamide and N-trimethylsilyl-N-methylacetamide. Mixtures of a plurality of different silylating agents, for example trimethylsilyl chloride/hexamethyidisilazane, are also possible.

The silylation of the ethylenically unsaturated urethane precursors, for example of formula (3), is advantageously performed in an aprotic organic solvent, both nonpolar and dipolar solvents being suitable. Examples of suitable solvents are aliphatic or aromatic hydrocarbons, for example benzene, toluene, xylene or xylene mixtures or cyclohexane, halogenated hydrocarbons, for example methylene chloride or chloroform, ethers, such as dioxane or tetrahydrofuran, and dipolar aprotic solvents, for example formamide, N,N-dimethylformamide, pyridine or acetonitrile. Preferred organic solvents are aromatic or aliphatic hydrocarbons, for example benzene, toluene, xylene or xylene mixtures or cyclohexane, and cyclic ethers, such as, especially, dioxane or tetrahydrofuran. Especially preferred solvents are benzene, xylene or xylene mixtures or, especially, toluene. Mixtures of different solvents are also possible. Furthermore, the addition of a non-volatile polymerisation inhibitor, for example di-tert-butyl-p-cresol, to the reaction mixture often proves beneficial.

The temperature used for the silylation depends primarily on the reactivity of the silylating agent and on the solvent used and may therefore vary within wide limits. Temperatures of from 0 to 60° C. or preferably from about 15 to about 50° C. have proved advantageous. The reaction times may likewise vary within wide limits, for example between about 15 minutes and 24 hours.

Depending on the silylating agent used, it may be advantageous to add an acid acceptor or an acid catalyst to the silylation mixture. The addition of acid acceptors is preferred when compounds of formula (4a) above, for example trimethylchlorosilane, are used as silylating agent. A suitable acid acceptor is, in principle, any compound having basic activity. Examples are organic amines, especially aliphatic or aromatic amines, for example pyridine and tri-$C_1$–$C_4$alkylamines, preferably triethylamine. The addition of acid catalysts is preferred when compounds of formula (4b) or (4c) above are used. As acid catalyst there may be used, for example, a compound of formula (4a) above, for example trimethylchlorosilane, or an organic acid, for example trichloroacetic acid.

The silylating agent is used in at least equimolar amounts or, preferably, in a molar excess of, for example, up to 100 mol % based on the urethane to be silylated. When the silylating agent is used in excess it is preferably present in a molar excess of from 5 to 50 mol % and especially from 5 to 30 mol %, in each case based on the urethane to be silylated. When an acid acceptor is used it is advantageously present in an approximately equimolar amount, based on the silylating agent.

The ethylenically unsaturated N-silylurethanes formed, which correspond, for example, to formula (5) above, may, after isolation and purification or alternatively directly without working up, be converted thermally, with removal of a silyl ether, into the desired isocyanates. The thermolysis is advantageously performed in an inert solvent, for example in one of the above-mentioned aliphatic or aromatic hydrocarbons, preferably in an aromatic hydrocarbon, such as benzene, toluene or xylene, and especially in toluene, at elevated temperature, which may be, for example, from 40 to 150° C., preferably from 70 to 120° C., especially from 80 to 100° C. It furthermore proves beneficial to carry out the reaction and/or working up in the presence of a non-volatile polymerisation inhibitor, for example di-tert-butyl-p-cresol.

The resulting compounds of formula (1) may be isolated from the reaction mixture and purified in a manner known per se, for example by distillation. The person skilled in the art will be aware that the reaction steps according to the invention and the working up of the reaction mixtures are generally performed under protective gas, for example under nitrogen or argon, because of the sensitivity of the end products and the silylated intermediates to moisture.

A preferred embodiment of the present invention relates to a process for the preparation of compounds of formula (1) above wherein x is the number 1, B is a radical of formula (2) wherein $B_1$ is linear or branched $C_2$–$C_8$alkylene and $R_1$ is hydrogen or methyl, which process comprises reacting a compound of formula (3) above wherein $R_2$ is ethyl or phenyl and $R_1$, B and x are as defined above with a silylating agent selected from the group consisting of alkylsilyl halides, alkylsilylamines, hexaalkyl-disilazanes and N-silylacetamides to form a compound of formula (5) above and directly, without working up, subjecting that compound to thermolysis at a temperature of from 70 to 120° C.

The urethane precursors, which correspond, for example, to formula (3) above, are known per se or can be obtained in a manner known per se.

The precursors of formula (3) above wherein x is the number 0 may be obtained, for example, by reacting a vinyl halide, for example vinyl bromide, with a carbamic acid ester, for example urethane.

Compounds of formula (3) wherein x is the number 1 can be obtained, for example, by reacting a compound of formula (6)

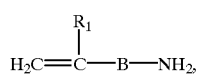

wherein B and $R_1$ are each as defined above, with a haloformic acid ester of formula (7)

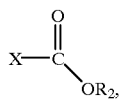

wherein X is halogen, preferably chlorine, and $R_2$ is as defined above.

The synthesis of compounds of formula (3) wherein B is a radical of formula (2) above may also be carried out advantageously by reacting a compound of formula (8)

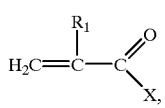

wherein X is halogen, preferably chlorine, and $R_1$ is as defined above, with a compound of formula (9)

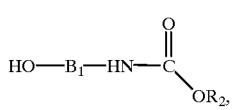

wherein $B_1$ and $R_2$ are each as defined above. The compounds of formulae (6), (7), (8) and (9) are all known or can be prepared using methods known per se.

A preferred embodiment of the present invention relates to a process for the preparation of compounds of formula (1a)

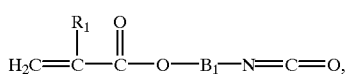

wherein $R_1$ is hydrogen or methyl and $B_1$ is linear or branched $C_2$–$C_{12}$alkylene that is uninterrupted or is interrupted by one or more oxygen atoms, which process comprises (a) reacting a compound of formula (6a)

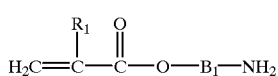

or preferably an acid addition salt, for example a hydrohalide, such as especially the hydrochloride, thereof, wherein $R_1$ and $B_1$ are each as defined above, with a haloformic acid ester of formula (7)

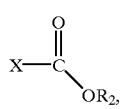

wherein X is halogen and $R_2$ is $C_1$–$C_4$alkyl or is phenyl that is unsubstituted or substituted by $C_1$–$C_4$alkyl, $C_1$–$C_4$alkoxy or by halogen, to form a compound of formula

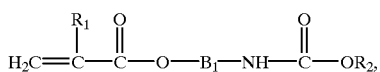
(3a)

(b) converting the urethane compound obtainable according to (a), with the aid of a silylating agent, into a compound of formula

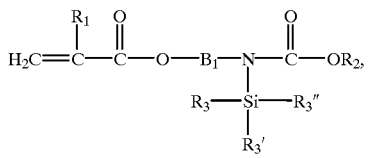
(5a)

wherein $R_3$, $R_3'$ and $R_3''$ are each independently of the others $C_1$–$C_4$alkyl and the variables $R_1$, $R_2$ and $B_1$ are as defined above, and (c) thermolytically converting the N-silylurethane compound obtainable according to (b) into a compound of formula (1).

A further preferred embodiment of the present invention relates to a process for the preparation of compounds of formula

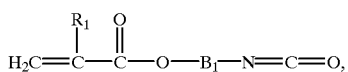
(1a)

wherein $R_1$ is hydrogen or methyl and $B_1$ is linear or branched $C_2$–$C_{12}$alkylene that is uninterrupted or is interrupted by one or more oxygen atoms, which process comprises (a) reacting a compound of formula

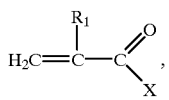
(8)

wherein $R_1$ is as defined above and X is halogen, with a compound of formula

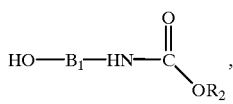
(9)

wherein $R_2$ is $C_1$–$C_4$alkyl or is phenyl that is unsubstituted or substituted by $C_1$–$C_4$alkyl, $C_1$–$C_4$alkoxy or by halogen and $B_1$ is as defined above, to form a compound of formula

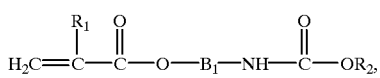
(3a)

(b) converting the urethane compound obtainable according to (a), with the aid of a silylating agent, into a compound of formula

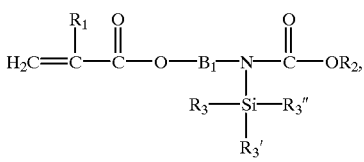
(5a)

wherein $R_3$, $R_3'$ and $R_3''$ are each independently of the others $C_1$–$C_4$alkyl and the variables $R_1$, $R_2$ and $B_1$ are as defined above, and (c) thermolytically converting the N-silylurethane compound obtainable according to (b) into a compound of formula (1).

The ethylenically unsaturated isocyanates that can be prepared by the process according to the invention and which may correspond, for example, to formula (1) above, can be used as starting materials for the preparation of a wide variety of products, for example in the field of pharmaceuticals or insecticides, or are used, especially, as monomers or comonomers in the preparation of polymerisates or copolymerisates. The compounds are especially useful in the synthesis of polymerisable macromers and macromonomers, as are used in the manufacture of numerous biomedical articles and materials, for example contact lenses.

The Examples that follow serve to illustrate the present invention in more detail; they are not, however, intended to limit the scope thereof in any way. Unless stated otherwise, temperatures are given in degrees Celsius.

Preparation of the urethanes of formula (3)

EXAMPLE 1

608 ml of ethanolamine are dissolved in 13 liters of dry methylene chloride under a nitrogen atmosphere in a reaction vessel and then 6.7 g of tetrabutylammonium bromide and 2378 g of sodium carbonate are added. The mixture is stirred until a homogeneous suspension is formed and it is cooled to 10° C. A mixture of 1402 ml of phenyl chloroformate in 5 liters of dry methylene chloride is then added dropwise within about 11 hours at a temperature of from 10 to 15° C. and the exothermic reaction which commences is controlled by cooling externally using ice. When the addition is complete, stirring is continued until the starting materials have been reacted completely (about 30 minutes at 25° C.). The resulting fine suspension is filtered and then concentrated to a volume of about 1 liter using a rotary evaporator. 5 liters of n-hexane are added and the resulting suspension is stirred overnight at room temperature (25° C.); the suspension is then cooled to 10° C. and the solid material is isolated by filtration. The resulting crystalline product is washed with two 500 ml portions of n-hexane and dried at 30° C. in vacuo. The compound N-(2-hydroxyethyl)-phenylcarbamate is obtained in the form of a white, crystalline product having a melting point of 79–80° C.

620.3 g of the N-(2-hydroxyethyl)-phenylcarbamate prepared above and 7.5 liters of methylene chloride are combined under a nitrogen atmosphere in a reaction vessel. 1000 ml of freshly distilled methacryloyl chloride are added to the resulting suspension. Heating at 80° C. is carried out overnight, with a gentle stream of argon protective gas being passed through the reaction vessel. A clear solution is formed, which is cooled to 25° C. and freed completely of the solvent using a rotary evaporator. The resulting crystalline solid is re-crystallised from a mixture of 5 liters of toluene and 3 liters of n-hexane, then washed with 500 ml of n-hexane and dried at 30° C. in vacuo. The compound N-(2-methacryloyloxyethyl)-phenylcarbamate is obtained in the form of a white, crystalline product having a melting point of 105–106° C.

EXAMPLE 2

In a reaction vessel thoroughly heated under dry nitrogen, 15.56 g of 2-aminoethyl methacrylate hydrochloride are dissolved in 30 ml of dry N,N-dimethylacetamide under a nitrogen atmosphere and the clear, light-yellow solution is cooled to about 4° C. Then, at that temperature, there are simultaneously added dropwise (a) a solution of 15.66 g of phenyl chloroformate in 50 ml of dry methylene chloride and (b) a solution of 20.5 g of triethylamine in 50 ml of dry methylene chloride. After 1.5 hours at about 4° C. the mixture is heated to room temperature and stirred for about 12 hours more. 15 mg of di-tert-butyl-p-cresol are added and the resulting white suspension is freed of most of the solvent using a rotary evaporator. The suspension is diluted by adding 200 ml of methylene chloride and extracted three times using 200 ml of water each time; the organic phase is then dried using sodium sulfate. After concentration by evaporation using a rotary evaporator the resulting residue is re-crystallised from diethyl ether/methylene chloride in a ratio of 4:1. The compound N-(2-methacryloyloxyethyl)-phenylcarbamate is obtained in the form of a white, crystalline product having a melting point of 110° C.

EXAMPLE 3

Using the procedure described in Example 1,18.1 g of N-(2-hydroxyethyl)-phenylcarbamate in dry methylene chloride are reacted with 9.05 g of acryloyl chloride and 10.1 g of triethylamine, yielding the compound N-(2-acryloyloxyethyl)-phenylcarbamate, which is re-crystallised from toluene/hexane.

Preparation of the isocyanates of formula (1)

EXAMPLE 4

400 g of the N-(2-methacryloyloxyethyl)-phenylcarbamate obtained according to Example 1 or 2 are suspended in 3 liters of dry toluene under argon protective gas with strict exclusion of moisture. After adding 240 g of dry triethylamine and 4 g of di-tert-butyl-p-cresol, the reaction mixture is heated to 50° C., and 204 g of freshly distilled trimethylsilyl chloride are added dropwise over a period of about 20 minutes. After 6 hours at 50° C., the silylation is complete and a fine suspension containing triethylammonium chloride has formed.

The thermal elimination of the phenoxy-trimethylsilane from the resulting N-silylated urethane is carried out by heating the suspension for about 8 hours under reflux (about 100° C.). The suspension is then stirred overnight at room temperature in order to cause the triethylammonium chloride to crystallise completely. For working up of the reaction mixture, a solution of 2 g of di-tert-butyl-p-cresol in 100 ml of dry toluene is added and low-boiling components (excess triethylamine, trimethylsilyl chloride) are then removed by distillation at about 80–100° C. After cooling to 25° C., the triethylammonium chloride is separated from the reaction suspension by filtration under an argon protective gas atmosphere and washed several times with dry toluene; the collected filtrates are concentrated to an amount of about 680 g using a rotary evaporator. That residue is first of all rapidly distilled at about 4–5 mbar without careful fractionation. The fractions having boiling points of between 60 and 80° C. are collected and, after addition of a further 2 g of di-tert-butyl-p-cresol, subjected to fractionation using a Vigreux column. The compound 2-isocyanatoethyl methacrylate is obtained in the form of a colourless oil having a boiling point of 60° C. at 7 mbar.

EXAMPLE 5

In a manner analogous to that described in Example 4, 47.6 g of the N-(2-acryl-oyloxyethyl)-phenylcarbamate prepared according to Example 3 are silylated in dry toluene using 22.8 g of trimethylchlorosilane and 21.2 g of triethylamine. The process is continued without isolation of the intermediate and, after the thermolysis and subsequent fractional distillation, the compound 2-isocyanatoethyl acrylate, which has a boiling point of 52–54° C. at 5 mbar, is obtained.

What is claimed is:

1. A process for preparing a compound of formula (1):

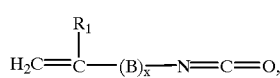

(1)

wherein $R_1$ is hydrogen or methyl, x is the number 0 or 1,

B is phenylene or $C_7$–$C_{12}$aralkylene each of which is unsubstituted or substituted by $C_1$–$C_4$alkyl or by $C_1$–$C_4$alkoxy or is a radical of formula

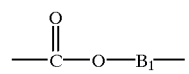

(2)

and $B_1$ is linear or branched $C_2$–$C_{12}$alkylene that is uninterrupted or is interrupted by one or more oxygen atoms, which process comprises converting an ethylenically unsaturated urethane of formula

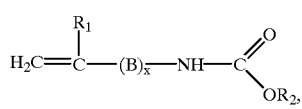

(3)

wherein $R_2$ is $C_1$–$C_4$alkyl or is phenyl that is unsubstituted or substituted by $C_1$–$C_4$alkyl, $C_1$–$C_4$alkoxy or by halogen and the variables $R_1$, B and x are as defined above, with the aid of a silylating agent, into an ethylenically unsaturated N-silyl-urethane of formula

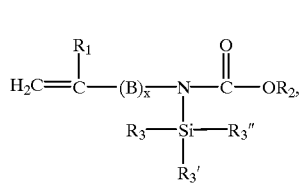

(5)

wherein $R_3$, $R_3'$ and $R_3''$ are each independently of the others $C_1$–$C_4$alkyl and the variables $R_1$, $R_2$, B and x are as defined above, and converting that compound at a temperature of from 70 to 120° C. into an ethylenically unsaturated isocyanate of formula (1).

2. A process according to claim 1, wherein x is the number 1.

3. A process according to claim 1, wherein x is the number 1 and B is a radical of formula (2).

4. A process according to claim 3, wherein $B_1$ is linear or branched $C_2$–$C_8$alkylene.

5. A process according to claim 1, wherein $R_2$ is $C_1$–$C_2$alkyl or is phenyl that is unsubstituted or substituted by methyl, methoxy or by chlorine.

6. A process according to claim 1, wherein the silylating agent is an alkylsilyl halide, alkylsilylamine, hexaalkyldisilazane or N-silylacetamide.

7. A process according to claim 1, wherein the silylating agent corresponds to formula

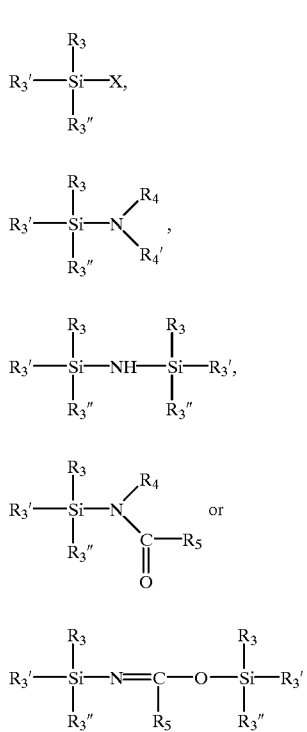

(4a)

(4b)

(4c)

(4d)

(4e)

wherein X is halogen, $R_3$, $R_3'$ and $R_3''$ are each independently of the others $C_1$–$C_4$alkyl, $R_4$ and $R_4'$ are each independently of the other hydrogen or $C_1$–$C_4$alkyl and $R_5$ is $C_1$–$C_4$alkyl.

8. A process according to claim 1, wherein the silylating agent is trimethylsilyl chloride, hexamethyldisilazane, N-trimethylsilyl-N, N-diethylamine, N,O-bis(trimethylsilyl) acetamide or N-trimethylsilyl-N-methylacetamide or a mixture of trimethylsilyl chloride and hexamethyldisilazane.

9. A process according to claim 1, wherein the silylation of the ethylenically unsaturated urethane is performed in an aprotic organic solvent at a temperature of from 15 to 50° C. under a protective gas atmosphere.

10. A process according to claim 1, wherein the ethylenically unsaturated N-silyl-urethane is converted thermally into the ethylenically unsaturated isocyanate directly, without working up.

11. A process according to claim 1, wherein the thermolysis of the ethylenically unsaturated N-silyl-urethane to form the ethylenically unsaturated isocyanate is performed in an aprotic solvent at a temperature of from 70 to 120° C. under a protective gas atmosphere.

12. A process according to claim 1 for the preparation of a compound of formula (1), wherein x is the number 1, B is a radical of formula (2) wherein $B_1$ is linear or branched $C_2$–$C_8$alkylene and $R_1$ is hydrogen or methyl, which process comprises reacting a compound of formula (3) wherein $R_2$ is ethyl or phenyl and $R_1$, B and x are as defined above, with a silylating agent selected from the group consisting of alkylsilyl halides, alkylsilylamines, hexaalkyl-disilazanes and N-silylacetamides to form a compound of formula (5) and directly, without working up, subjecting that compound to thermolysis at a temperature of from 70 to 120° C.

13. A process according to claim 12, wherein $R_2$ is phenyl and the thermolysis is carried out at a temperature of from 80 to 100° C.

14. A process for the preparation of a compound of formula

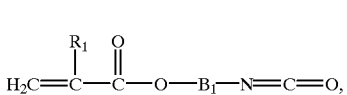

(1a)

wherein $R_1$ is hydrogen or methyl and $B_1$ is linear or branched $C_2$–$C_{12}$alkylene that is uninterrupted or is interrupted by one or more oxygen atoms, which process comprises (a) reacting a compound of formula

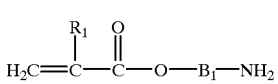

(6a)

or an acid addition salt thereof, wherein $R_1$ and $B_1$ are each as defined above, with a haloformic acid ester of formula

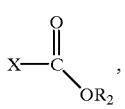

(7)

wherein X is halogen and $R_2$ is $C_1$–$C_4$alkyl or is phenyl that is unsubstituted or substituted by $C_1$–$C_4$alkyl, $C_1$–$C_4$alkoxy or by halogen, to form a compound of formula

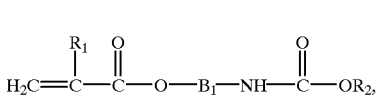

(3a)

(b) converting the urethane compound obtainable according to (a), with the aid of a silylating agent, into a compound of formula

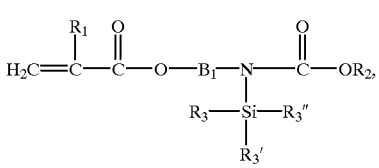

(5a)

wherein $R_3$, $R_3'$ and $R_3''$ are each independently of the others $C_1$–$C_4$alkyl and the variables $R_1$, $R_2$ and $B_1$ are as defined above, and (c) converting the N-silylurethane compound obtainable according to (b), by means of thermolysis, into a compound of formula (1).

15. A process for the preparation of a compound of formula

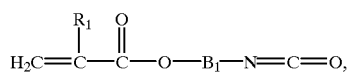 (1a)

wherein $R_1$ is hydrogen or methyl and $B_1$ is linear or branched $C_2$–$C_{12}$alkylene that is uninterrupted or is interrupted by one or more oxygen atoms, which process comprises (a) reacting a compound of formula

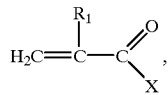 (8)

wherein $R_1$ is as defined above and X is halogen, with a compound of formula

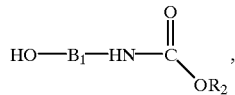 (9)

wherein $R_2$ is $C_1$–$C_4$alkyl or is phenyl that is unsubstituted or substituted by $C_1$–$C_4$alkyl, $C_1$–$C_4$alkoxy or by halogen and $B_1$ is as defined above, to form a compound of formula

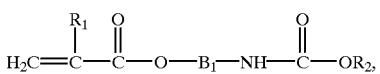 (3a)

(b) converting the urethane compound obtainable according to (a), with the aid of a silylating agent, into a compound of formula

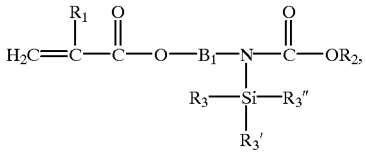 (5a)

wherein $R_3$, $R_3'$ and $R_3''$ are each independently of the others $C_1$–$C_4$alkyl and the variables $R_1$, $R_2$ and $B_1$ are as defined above, and (c) converting the N-silylurethane compound obtainable according to (b), by means of thermolysis, into a compound of formula (1).

* * * * *